(12) United States Patent
Malaney et al.

(10) Patent No.: US 6,493,588 B1
(45) Date of Patent: Dec. 10, 2002

(54) ELECTRO-NERVE STIMULATOR SYSTEMS AND METHODS

(75) Inventors: James Malaney, Iowa City; Robert A. Morris, Solon, both of IA (US); Marshall A. Stoller, San Francisco; Curtis A. Gleason, Palo Alto, both of CA (US)

(73) Assignee: MMC/GATX Partnership No. 1, Lafayette, CA (US)

( * ) Notice: Subject to any disclaimer, the term of this patent is extended or adjusted under 35 U.S.C. 154(b) by 0 days.

(21) Appl. No.: 09/213,558

(22) Filed: Dec. 17, 1998

Related U.S. Application Data

(60) Provisional application No. 60/078,413, filed on Mar. 18, 1998.

(51) Int. Cl.[7] .................................................. A61N 1/34
(52) U.S. Cl. ........................................ 607/46; 607/72
(58) Field of Search ........................... 607/37, 41, 40, 607/46, 50, 51, 63, 72, 116; 439/909

(56) References Cited

U.S. PATENT DOCUMENTS

| | | | | |
|---|---|---|---|---|
| 3,893,462 A | | 7/1975 | Manning | 128/421 |
| 3,995,644 A | * | 12/1976 | Parsons | 607/116 |
| 4,406,288 A | * | 9/1983 | Horwinski et al. | 607/41 |
| 4,519,394 A | * | 5/1985 | Black et al. | 607/50 |
| 4,535,785 A | * | 8/1985 | Van Den Honert et al. | 600/559 |
| 5,056,518 A | * | 10/1991 | Pethica et al. | 607/2 |
| 5,094,242 A | | 3/1992 | Gleason et al. | 128/642 |
| 5,562,710 A | * | 10/1996 | Olsen et al. | 607/5 |
| 5,679,022 A | * | 10/1997 | Cappa et al. | 439/502 |
| 5,695,495 A | | 12/1997 | Ellman et al. | 606/41 |
| 5,782,892 A | * | 7/1998 | Castle et al. | 607/37 |
| 5,906,634 A | * | 5/1999 | Flynn et al. | 607/37 |
| 5,954,758 A | * | 9/1999 | Peckham et al. | 607/48 |
| 6,141,585 A | * | 10/2000 | Prutchi et al. | 607/8 |

FOREIGN PATENT DOCUMENTS

| | | | |
|---|---|---|---|
| WO | WO 97/49453 | 12/1997 | A61N/1/36 |

OTHER PUBLICATIONS

SANS "Examine the revolutionary SANS™ device at EAU Stand 9.05.," UroSurge (1998).
SANS "Introducing an innovative point of treatment for urge incontinence," UroSurge (1998).
SANS "Introducing two New Treatments for Stress and Urge Incontinence," UroSurge (1998).
SANS "Bold innovations in urology. Visit UroSurge at the EAU Convention.," UroSurge (1998).
"Sacral Nerve Stimulation Improves Chronic Voiding Dysfunction Symptoms," Medtronic (undated).

(List continued on next page.)

Primary Examiner—Kennedy Schaetzle
(74) Attorney, Agent, or Firm—Dorsey & Whitney LLP; Scott D. Rothenberger

(57) ABSTRACT

An electro-nerve stimulator system includes a pulse generator for generating current pulses with a transcutaneous patch and percutaneous needle for delivering current pulses to selected stimulation sites. The stimulator is a small battery operated external device that allows adjustment of stimulation levels and interfaces, via a connector, to the transpercutaneous cable. The transcutaneous electrode is attached to the skin distal from the desired stimulated nerve site. A percutaneous needle is inserted close to the internal nerve site. Stimulation current pulses are designed to flow between the transcutaneous electrode and the internal percutaneous needle. The field generated at the needle site causes the nerve to fire.

10 Claims, 6 Drawing Sheets

OTHER PUBLICATIONS

Stoller, M.L., "Needle Stimulation (through the skin) for the Treatment of Incontinence," Quality Care, vol. 16, No. 1 (Winter 1998), pp. 1–2 (mailed Feb. 1998).

Stoller M.L. et al, "The Efficacy of Acupuncture in Reversing the Unstable Bladder in Pig–Tailed Monkeys,"0 AM Urological, (1998).

Bolz, A., "Die Bedeutung Der Phasengrenze Zwischen Alloplastischen Festkorpern Und Biologischen Geweben Fur Die Elektrostimulation," pp. 11–15 (Feb. 1995).

Urbaszek, A., "Konzeption Und Technische Losungen Zur Optimierung Der Frequenzadaptiven Elektrostimulation Des Herzens," pp. 23–25 (May 1995).

* cited by examiner

ELECTRO-NERVE STIMULATOR SYSTEMS AND METHODS

REFERENCE TO RELATED APPLICATION

This application claims the benefit of U.S. Provisional Application No. 60/078,413, filed on Mar. 18, 1998 and incorporated herein by reference.

BACKGROUND OF THE INVENTION

Physical therapists, chiropractors, and other medical providers have used nerve and muscle stimulation to treat a variety of ailments. These medical providers have used electronic muscle stimulation (EMS) and transcutaneous electrical nerve stimulation (TENS) as a treatment for muscle and joint rehabilitation as well as chronic pain. Urologists and obstetrician/gynecologists have used a form of TENS for pelvic floor stimulation to treat incontinence and pelvic pain. In addition, medical providers have used a variety of implantable and percutaneous stimulators to manage pain, to create local nerve blocks, and to treat incontinence, Parkinson's disease, and multiple sclerosis.

Transcutaneous stimulators, i.e., stimulators which do not physically penetrate the skin surface, are less invasive than percutaneous and implantable stimulators. However, transcutaneous stimulators often require higher current levels than percutaneous and implantable stimulators. Higher current levels can cause irritation and discomfort when used for extended periods. Also, since transcutaneous stimulators stimulate on the skin surface, their target site usually covers a large area. Thus, transcutaneous stimulators may not be highly effective for direct nerve stimulation.

More typically, providers use implantable stimulators when there is a need for direct nerve stimulation or continuous stimulation. Implantable stimulators can free a patient from the need for constant and frequent manual treatment. However, implantable stimulators can cause mild discomfort, and often cause more severe implant-site pain.

Percutaneous stimulators provide direct nerve stimulation without the invasiveness of an implant. However, traditional percutaneous stimulators need to be in close proximity to a target nerve. Movement of the stimulating needle can result in a loss of the ability to stimulate a target nerve. A medical provider often needs to re-insert and/or re-locate the percutaneous needle during treatment. In addition, the load impedance provided by sub-cutaneous tissue is low. Such low impedance can result in unwanted or accidental transmission of relatively high current levels. Such relatively high current levels can result in nerve and tissue damage.

It is an object of the invention to provide stimulator systems and methods that provide the non-invasiveness of transcutaneous systems with the effectiveness of percutaneous systems.

It is another object of the invention to provide systems and methods that are less likely to result in nerve and tissue damage.

It is yet another object of the invention to provide inexpensive and durable electro-nerve stimulation systems.

Other general and more specific objects of this invention will in part be obvious and will in part be evident from the drawings and the description which follow.

SUMMARY OF THE INVENTION

In one aspect, the present invention is directed to transcutaneous-percutaneous electro-nerve stimulator systems and methods that are minimally invasive and that are effective in direct nerve stimulation. A system according to one aspect of the invention includes a pulse generator, a transcutaneous electrode electrically coupled to the pulse generator, and a percutaneous electrode electrically coupled to the pulse generator and having an end for insertion into a patient's body. The pulse generator produces pulses which couple between the transcutaneous electrode and the percutaneous needle. The transcutaneous electrode is positioned proximate to the selected stimulation site on the surface of the skin. Preferably, the transcutaneous electrode is positioned distal from the stimulation site. The percutaneous electrode is inserted through the skin in proximity to an internal stimulation site, preferably in proximity to the nerve to be stimulated. The pulses from the pulse generator traverse the internal stimulation site by passing between the transcutaneous electrode and the internal percutaneous electrode.

In another aspect of this invention, the transcutaneous electrode allows for maximum current dispersion at the application site. In one embodiment, an internal layer of the electrode is coated with a high conductive metal, such as silver, to disperse the stimulating current quickly over the entire electrode surface.

In another aspect of this invention, since the direction of the electric field can reduce the required intensity, the system includes a mechanism to assure a particular polarity of the stimulating current. According to this aspect of the invention, the system has a transcutaneous electrode that is fixedly attached to the first lead wire. In addition, the first and second lead wires are combined at one end into a single cable for interfacing with the pulse generator. The cable is "keyed" to interface with the pulse generator so that the transcutaneous electrode is always positive and the percutaneous electrode is always negative. In other words, the cable can be plugged into the pulse generator in only one way.

In another aspect of this invention, the electrical circuit of the pulse generator has an AC coupled current pulse output, and includes an element for measuring the amount of current delivered directly to the patient. Patient stimulators are safest when the output circuitry is AC coupled. AC coupled circuits guarantee that no net DC current will pass to the body. Traditional stimulators have accomplished an AC coupled output using a current transformer. A system according to one embodiment of the present invention includes circuitry which creates an AC coupled output without the need for a current transformer by using a DC blocking capacitor in conjunction with the following circuit features: a pulse shaping circuit, a DC-DC step up voltage source, a switching circuit, and a current sense/stimulation adjustment feedback control.

In another aspect of this invention, the circuitry includes a discharge path for the DC blocking capacitor which has an optimal discharge time-constant to accommodate the desired pulse width, duty cycle, and expected load range of the output pulse. A capacitor can serve as a DC block yet pass current pulses with sufficiently fast rise and fall times. However, after a number of pulses the capacitor can become charged if a discharge path is not provided. This accumulated charge voltage effectively subtracts from the available supply voltage so little or no pulse energy is delivered to the load. The discharge path in this circuitry is preferably designed to minimize droop during the output pulse yet assure full discharge by the time of the next pulse arrives.

In another aspect of this invention, the pulse generator circuitry includes the option of an active or passive discharge configuration. In the passive configuration, a discharge resistor can be included in the output circuit parallel to the DC blocking capacitor and output load. In the active configuration, a transistor type switch can be used to discharge the blocking capacitor. The switch can momentarily discharge the capacitor when the output pulse is not active.

In another aspect of this invention, the electrical output circuit has the frequency and pulse width fixed to a value optimal for a given application. The electrical output circuit only allows a user to adjust the stimulation current threshold. Thus the electrical output circuit prevents the user from setting the parameters to values that are sub-optimal or even harmful while making the device easier to use.

In another aspect of this invention, the percutaneous electrode can be in the form of a needle having a portion coated or insulated to allow for more precise stimulation points. In one embodiment, a portion of the needle shaft is covered or coated with an electrically-insulating material, while the needle tip is exposed to permit electrical contact with the patient's tissue.

In another aspect of this invention, the pulse generator is battery powered and is small enough to be comfortably worn or carried by the patient. For example, the pulse generator can be small enough to be worn around a leg or other body extremity using a small wrap similar to a blood pressure cuff.

BRIEF DESCRIPTION OF THE DRAWINGS

These and other features and advantages of the present invention will be more fully understood by reference to the following detailed description in conjunction with the attached drawings in which like reference numerals refer to like elements and in which.

DETAILED DESCRIPTION

Figure 1:
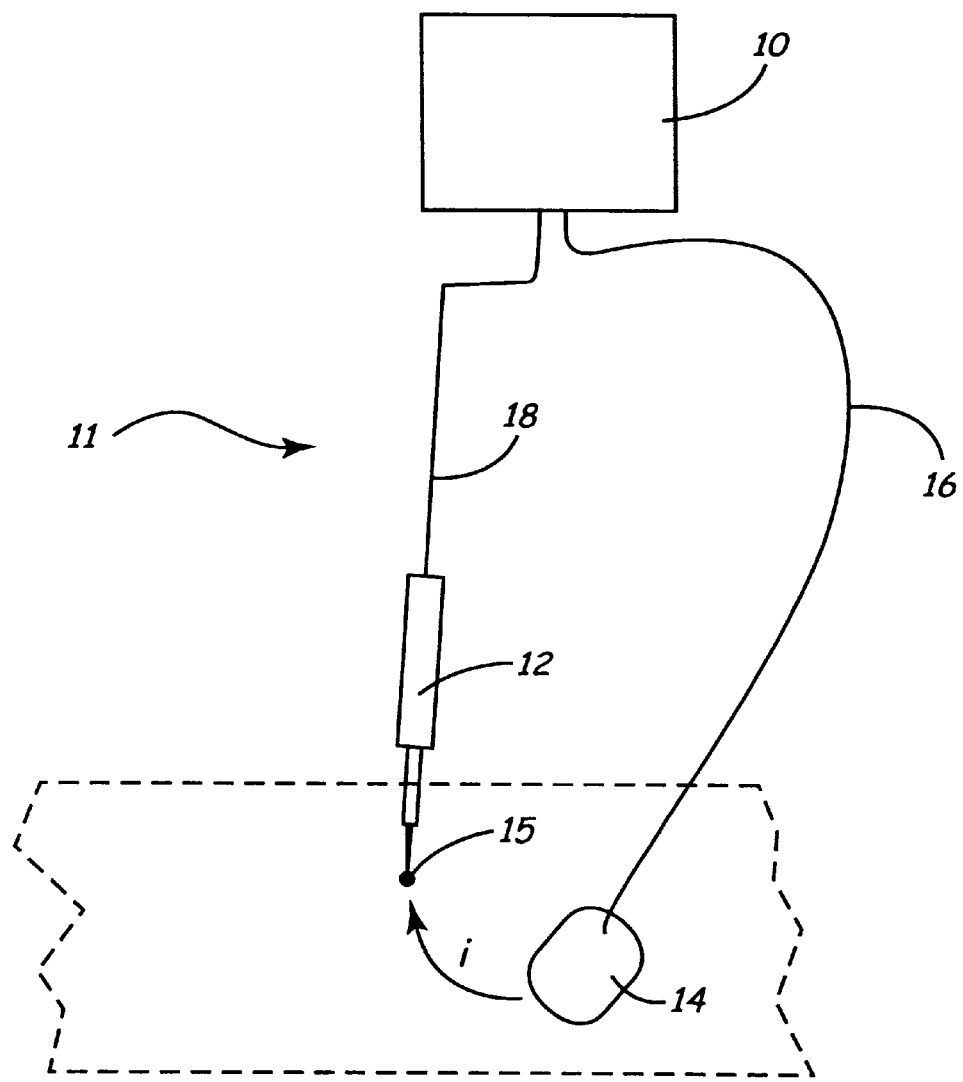
FIG. 1 is a schematic illustration of the components of a electro-nerve stimulation system according to one embodiment of the invention.

FIG. 1 shows one embodiment of a combined transcutaneous-percutaneous stimulator system according to the invention. The system 11 includes a pulse generator 10, a first lead wire 16 electrically coupled to the pulse generator 10, a transcutaneous electrode 14 electrically coupled to the first lead wire 16, a second lead wire 18 electrically coupled to the pulse generator 10, and a percutaneous electrode needle 12 electrically coupled to the second lead wire 18.

Figure 1A:
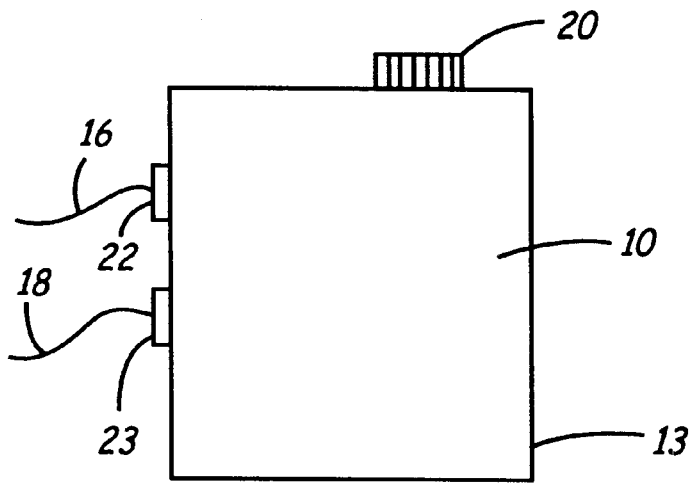
FIG. 1A is a schematic illustration of a pulse generator of the electro-nerve stimulation system of FIG. 1 according to one embodiment of the invention.

A pulse generator 10 according to one aspect of the invention is illustrated in FIG. 1A and includes an electrically isolating housing 13 for electronic components and connector ports 22, 23 for the first and second lead wires 16, and 18, respectively. Alternatively, the lead wires can be combined into a single cable at one end for interfacing with a single interface on the pulse generator. The pulse generator 10 can include an On/Off switch and an intensity control 20.

Referring again to FIG. 1, according to one embodiment of the invention, the pulse generator 10 is a small hand-held, battery operated pulse generator that produces small current pulses which pass between a transcutaneous electrode 14 and a percutaneous needle 12. The electrode 14 is positioned 'down-stream', i.e., distal, from the selected stimulation site 15 on the surface of the skin. The percutaneous electrode needle 12 is inserted through the skin at a location and to a depth that brings the tip in close proximity to a nerve or nerves to be stimulated. Current pulses traverse the internal stimulation site by passing from the transcutaneous electrode 14 to the internal percutaneous electrode needle 12, as indicated by arrow i in FIG. 1.

Advantageously, the current density and subsequent electric field intensity generated between the surface electrode and the percutaneous needle is greater than that generated by traditional percutaneous stimulators. A greater electric field intensity makes site location for the transcutaneous electrode and percutaneous needle easier. Furthermore, the load impedance through the surface of the skin is much higher than the internal impedance. This relatively high load impedance lessens the likelihood of damage to tissue and nerves due to high current pulses. The transcutaneous electrode also creates a capacitive interface which attenuates harmful DC currents. Moreover, the system, according to one embodiment of the invention, has only one percutaneous needle, which lessens the invasiveness of the nerve stimulation procedure.

The system 11 of the present invention is particularly suited for the treatment of urinary urge incontinence in accordance with the following exemplary procedure. The transcutaneous electrode 14 is placed on a patient's skin distal to the selected stimulation site 15. The percutaneous needle 12 is then positioned to penetrate the patient's skin and is advanced into proximity with the stimulation site 15. The pulse generator 10 is then activated to generate current pulses. The current pulses from the pulse generator 10 traverse the internal stimulation site 15 by passing from the transcutaneous electrode 14 to the percutaneous needle 15.

Those skilled in the art will appreciate that the nerve stimulation system of the present invention is effective not only for the treatment of urge incontinence, but can also be effective for both nerve and muscle stimulation to treat other numerous conditions, including, for example, muscle and joint rehabilitation, chronic pain, Parkinson's disease, and multiple sclerosis. In addition, the system can be used to manage pain and create local nerve blocks, as well as in any other application in which it is desirable to provide electrical nerve and/or muscle stimulation.

Figure 1B:
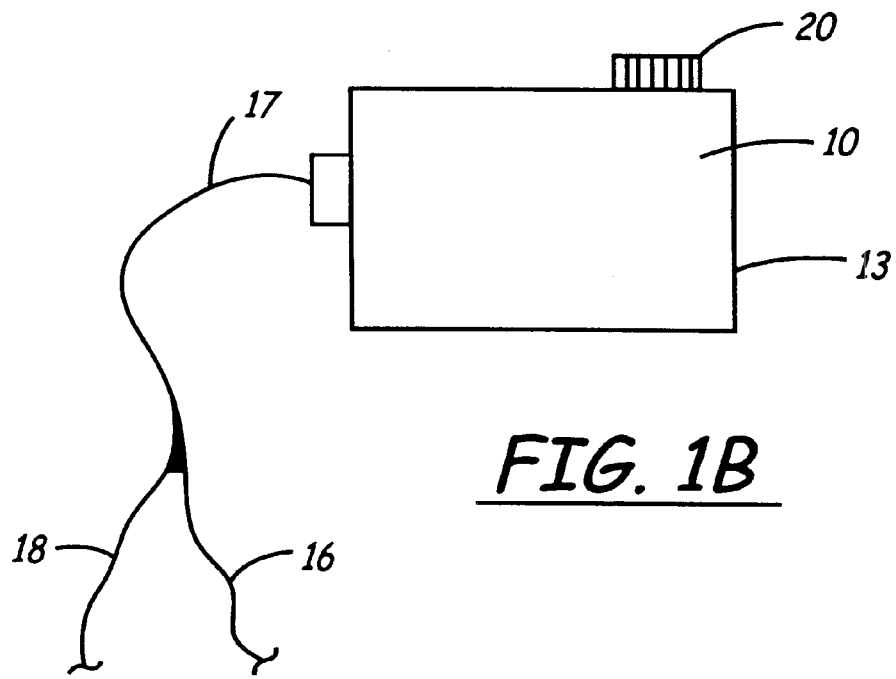
FIG. 1B is a schematic illustration of a pulse generator of the electro-nerve stimulation system of FIG. 1 according to a second embodiment of the invention.

The current intensity required to produce a desired result, e.g., symptomatic relief to a patient, can vary at least in part, based on the direction of the electric field. Thus, the system 11 can include a mechanism to assure a particular polarity of the stimulating current. This can be accomplished by pre-attaching the transcutaneous electrode 14 to the first lead wire 16 and combining the first and second lead wires 16, 18 into a single cable 17 at one end for interfacing with the pulse generator 10, as illustrated in FIG. 1B. Additionally, the cable 17 can be 'keyed' to prevent plugging the cable in backwards. With these safeguards, during a current pulse, current flows from the transcutaneous electrode to the percutaneous needle.

The pulse generator 10 preferably has an AC coupled current pulse output and can include an element for measuring the amount of current delivered directly to the patient. Patient stimulators are safest when the output circuitry is AC coupled. AC coupled circuits ensure that no net DC current will pass to a patient's body. Traditional stimulators have often accomplished AC coupling using current transformers. However, a transformer is often large and heavy. The stress caused by a transformer on a circuit board and internal supporting structures can cause circuit failures. The transformer output circuit usually measures primary current and does not actually measure the delivered secondary current.

Figure 2:
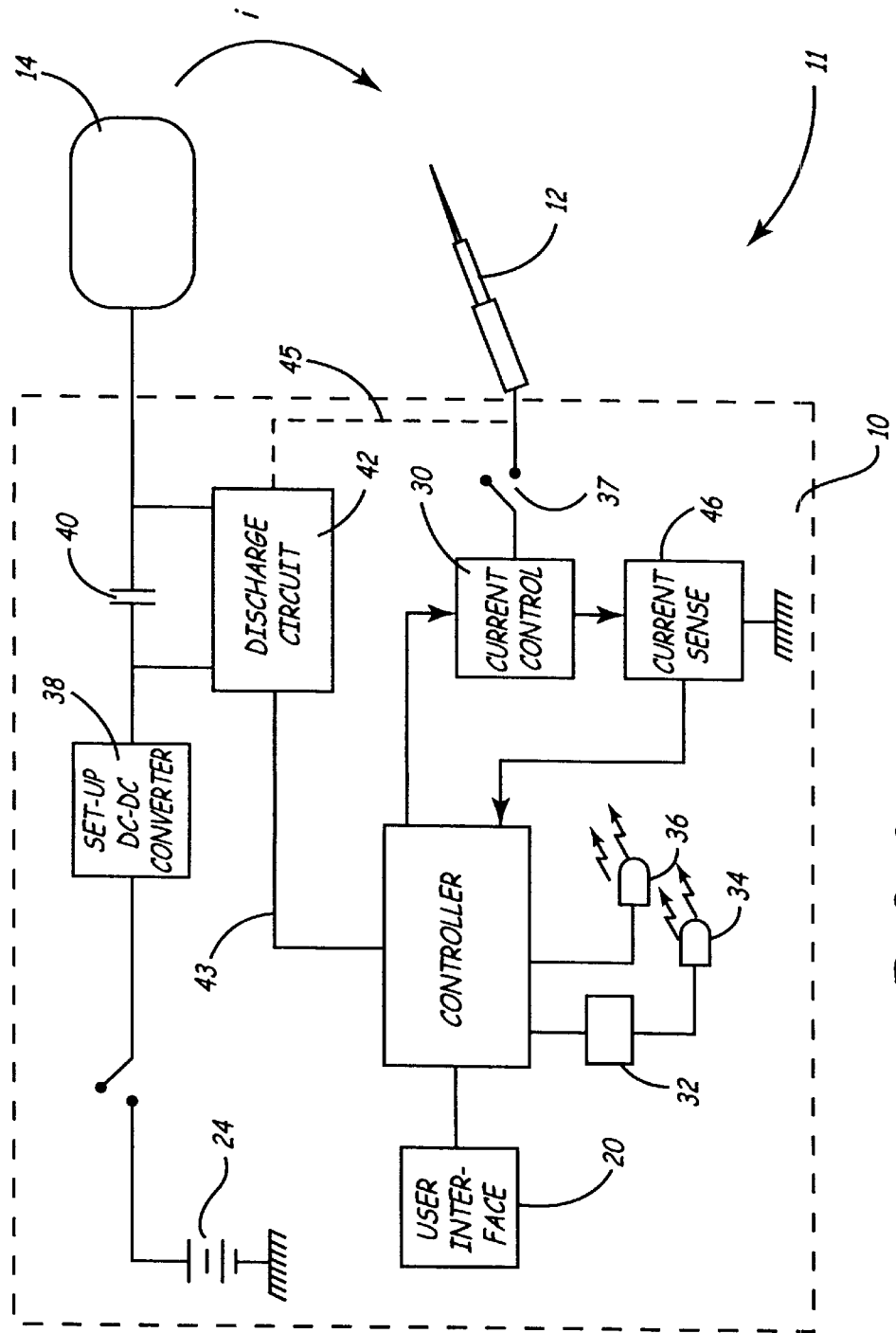
FIG. 2 is a block diagram of the circuitry of the pulse generator of FIG. 1.

With reference to FIG. 2, one embodiment of this invention includes circuitry which creates an AC coupled output without the need for a current transformer by using a DC blocking capacitor 40 in conjunction with the following circuit features: a current control 30 preferably including a pulse shaping circuit, a step-up DC-DC voltage converter 38, a switching circuit 37, and a current sense/stimulation adjustment feedback control 46. As a result, the pulse generator 10 is a current source. A controller 44, such as a MAX773 integrated circuit, available from Maxim Integrated Products of Sunnyvale, Calif., controls the operation of the pulse generator 10, including serving as a feedback controller for the DC-DC converter 38 and driving a low voltage detector 32. A low voltage indicator 34 and On/Off indicator 36 are also driven by controller 44. The sense/stimulation adjustment feedback control 46 can measure actual current delivered to the patient's skin. In addition, the patient intensity control adjust 20 allows the patient to adjust the delivered current.

The pulse generator 10 can include a discharge path in the form of a discharge circuit 42 for the DC blocking capacitor 40. The discharge circuit 42 has an optimal discharge time-constant to accommodate the desired pulse width, duty cycle, and expected load range of the output pulse. A capacitor, such DC blocking capacitor 40, can serve as a DC block yet pass current pulses with sufficiently fast rise and fall times. However, after a number of pulses the capacitor can become charged if a discharge path is not provided. This accumulated charge voltage effectively subtracts from the available supply voltage so little or no pulse energy is delivered to the load. The discharge path in this embodiment minimizes droop during the output pulse yet assure full discharge by the time of the next pulse arrives.

The discharge circuit 42 can be provided in an active or passive discharge configuration. In the active configuration, a transistor type switch 112, such as BSS123LT available from Motorola, Inc., is used to discharge the blocking capacitor 140, as illustrated in FIG. 2B. The switch 140 can momentarily discharge the capacitor when the output pulse is not active. During active discharge, discharge circuit 42 can be controlled by controller 44 through electrical connection 43 (FIG. 2).

Figure 2A:
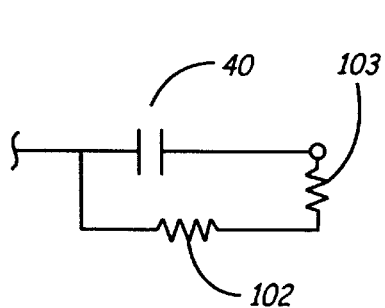
FIG. 2A is a schematic diagram of the blocking capacitor and a passive discharge circuit of the pulse generator of the electro-nerve stimulation system of FIG. 1.
Figure 2B:
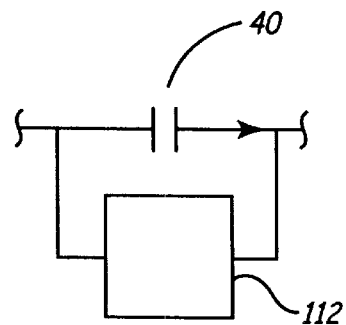
FIG. 2B is a schematic diagram of the blocking capacitor and an active discharge circuit of the pulse generator of the electro-nerve stimulation system of FIG. 1.

In the passive configuration, a discharge resistor 102 is included in the output circuit parallel to the DC blocking capacitor and across output load 103 through the percutaneous electrode, as illustrated in FIG. 2A. During passive discharge, discharge circuit 42 is coupled (shown as dashed line 45 in FIG. 2) to percutaneous needle 12 as well as to transcutaneous electrode 14. Controller 44 does not interact with discharge circuit 42 in the passive discharge configuration and connection 43 need not be present.

The pulse generator 10, through the current sense/stimulation adjustment feedback control 46, can have the frequency and pulse width fixed to a value optimal for a given application and only allow the user adjustment of the stimulation current threshold. This prevents the user from setting the parameters to values that are suboptimal while making the device easier to use when compared to stimulators that allow adjustment of both frequency and pulse width.

The pulse generator 10 is preferably battery powered through battery 24 and is preferably small enough to be comfortably worn or carried by the patient. For example, the pulse generator can be small enough to be worn around a leg or other body extremity using a small wrap similar to a blood pressure cuff. Further, the pulse generator can be small enough to be hand held, belt-mounted, or pocket size.

Figure 3:
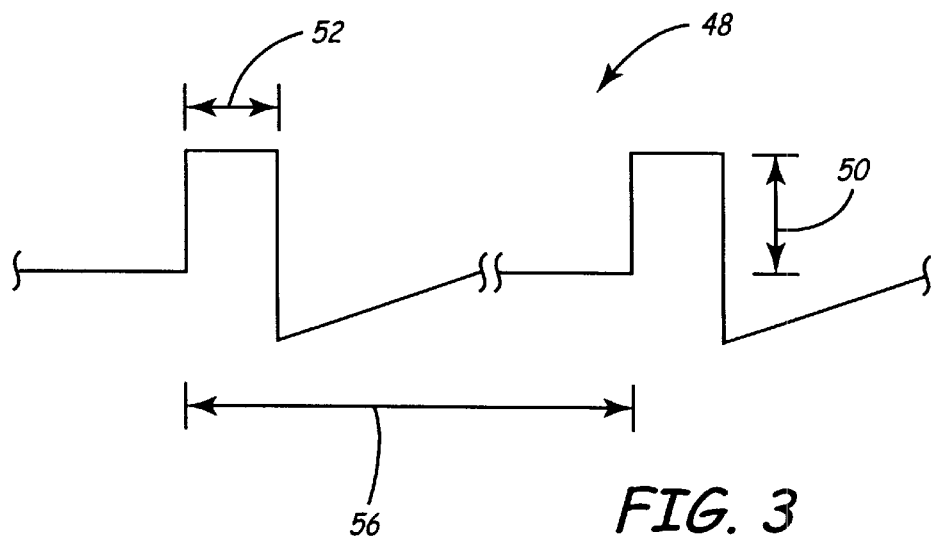
FIG. 3 is the output current waveform from the stimulation system of FIG. 1.

With reference to FIG. 3, a preferred output waveform 48 produced by a pulse generator according to one embodiment of the invention has a pulse width 52 of 100–300 sec, a pulse intensity 50 of 1–10 mA, and a pulse cycle time 56 of 20–80 msec. It will be appreciated that a pulse generator 10 according to one embodiment of the invention can provide other waveforms, having different pulse widths, pulse cycle times, or pulse intensities, to achieve a therapeutic result.

Figure 4:
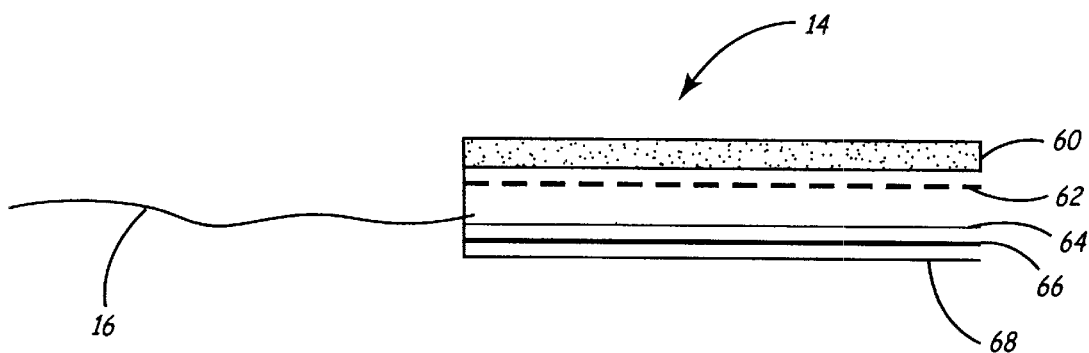
FIG. 4 shows a cross-sectional view of the transcutaneous electrode of FIG. 1.

With reference to FIG. 4, the transcutaneous electrode 14 according to one embodiment of the invention is designed for maximum signal dispersion by having the internal contact layer 64 coated with a high conductive material, such as silver. Traditional electrodes, used in monitoring applications, do not have a highly conductive internal layer. The absence of a highly conductive internal layer is less important for high input impedance monitoring circuits since they experience small current flow. For larger current level stimulators, however, hot spots can result if the electrode is constructed out of low conductivity materials.

Thus, in a preferred embodiment, the transcutaneous electrode is constructed to have high conductivity, e.g., to avoid "hot spots." FIG. 4 shows a transcutaneous electrode 14 with an attached lead wire 16 and including a series of layers including non-conductive foam 60, pressure sensitive adhesive 62, silver 64, carbon film 66, and biocompatible hypoallergenic hydrogel 68. These layers are pressed or sandwiched together to form transcutaneous electrode 14.

Figure 5:
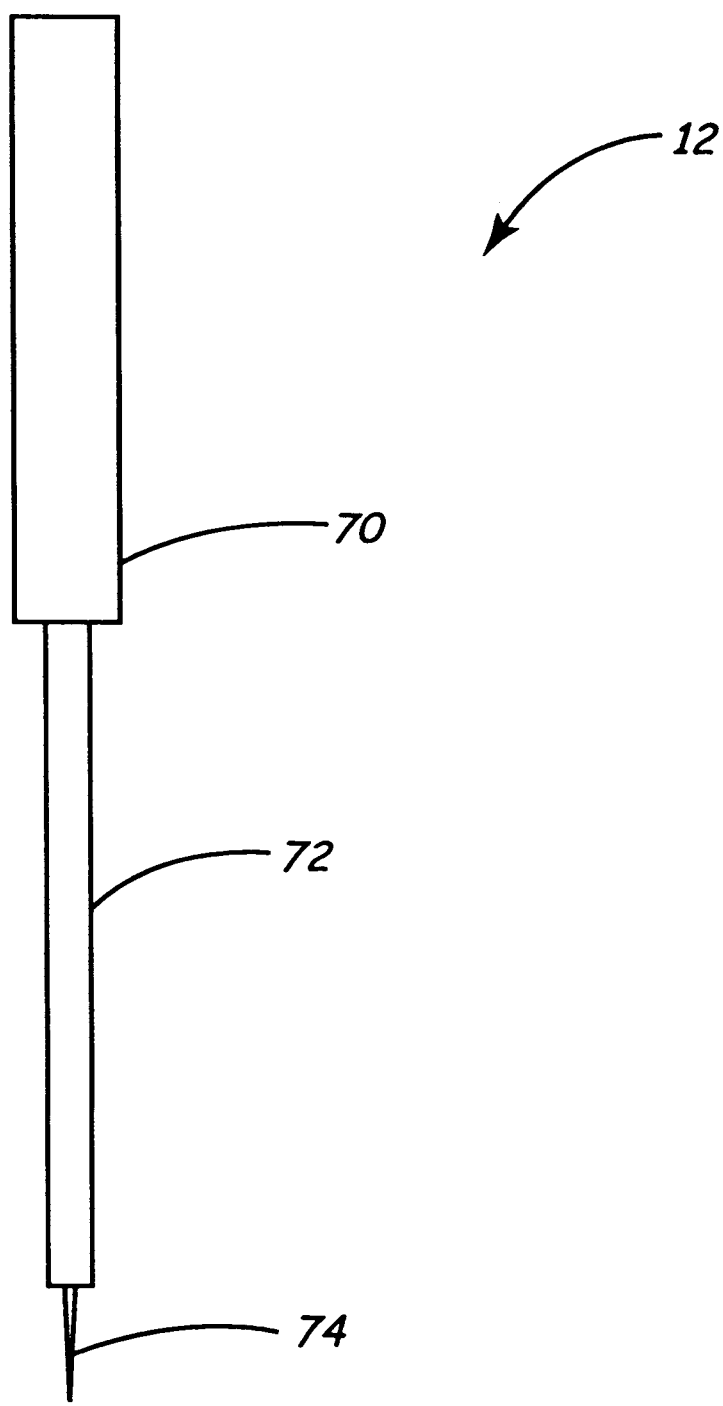
FIG. 5 shows a cross-sectional view of the percutaneous needle of FIG. 1.

With reference to FIG. 5, the illustrated percutaneous electrode needle 12 is constructed out of medical grade stainless steel or other biocompatible metal. The needle diameter is preferably small (less than 0.24 mm) which minimizes trauma during insertion. Part of the extended needle can consist of a metal or plastic handle 70, e.g., to provide a secure grip for the user, while minimizing the risk of shock to the user.

In another aspect of the invention, the needle preferably can be coated with Teflon or similar insulative material 72 except for an exposed tip area 74. This allows for a higher field density at the tip for more precise operation. The exposed needle tip area should have a sufficiently large surface area so as not to create too high a local current field that may cause irritation or pain. For example, the needle tip can have a terminal portion (exposed tip) 74 which extends between 0.5 and 10 mm and preferably 2.0 mm from the needle tip.

It will thus be seen that the objects set forth above, among those made apparent from the preceding description, are officially attained. Since certain changes may be made in the above constructions without departing from the scope of the invention, it is intended that all matter contained in the above description and shown in the accompanying drawings be interpreted as illustrative and not in a limiting sense.

It is also to be understood that the following claims are intended to cover all generic and specific features of the invention described herein, and all statements of the scope of the invention which as a matter of language might be the to fall therebetween.

Having described the invention, what is claimed as new and secure by Letters Patent is:

1. An apparatus for electro-nerve stimulation, the apparatus comprising:
    a pulse generator, wherein the pulse generator includes a DC blocking capacitor electrically coupled to a transcutaneous electrode, a battery for providing current, an oscillator circuit means electrically coupled to the battery for providing current pulses, pulse shaping means electrically coupled to the oscillator circuit means for shaping the current pulses from the oscillator circuit means, DC-DC step up voltage means electrically coupled to the battery and the DC blocking capacitor for changing a DC voltage provided by the battery, and feedback control means electrically coupled to a percuanteous needle and to the pulse shaping means for adjusting the current,
    a transcutaneous electrode electrically coupled to the pulse generator for delivering pulses from the pulse generator to a patient's skin, and
    a percutaneous electrode electrically coupled to the pulse generator and having an end for insertion into a patient's body in proximity to an internal stimulation site to receive pulses from the transcutaneous electrode.

2. The apparatus of claim 1, wherein the transcutaneous electrode includes a layer of a highly conductive metal.

3. The apparatus of claim 2, wherein the highly conductive metal is silver.

4. The apparatus of claim 1, wherein the pulse generator is a current source and generates current pulses.

5. The apparatus of claim 1, wherein the pulse generator further includes a discharge path for the DC blocking capacitor.

6. The apparatus of claim 5, wherein the discharge path includes an active circuit.

7. The apparatus of claim 6, wherein the active circuit includes a switch for providing a momentary discharge path across the DC blocking capacitor and a switch activation means for activating the switch in synchronization with the current pulses.

8. The apparatus of claim 5, wherein the discharge path includes a passive circuit.

9. The apparatus of claim 8, wherein the passive circuit includes a resistor electrically coupled to the DC blocking capacitor to provide a discharge path for the DC blocking capacitor.

10. The apparatus according to claim 9, wherein the DC blocking capacitor has a selected capacitance and the resistor has a selected resistance such that the time constant of the resistor coupled to the capacitor results in discharge of the capacitor between the pulses without causing substantial degradation of the pulses.

* * * * *